(12) United States Patent
Bodlaender et al.

(10) Patent No.: US 9,572,740 B2
(45) Date of Patent: Feb. 21, 2017

(54) INCUBATOR ILLUMINATION (75) Inventors: Maarten Peter Bodlaender, Eindhoven (NL); Willem Verkruijsse, Veldhoven (NL); Marek Janusz Bartula, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 377 days.

(21) Appl. No.: 14/343,425

(22) PCT Filed: Aug. 29, 2012

(86) PCT No.: PCT/IB2012/054423
§ 371 (c)(1),
(2), (4) Date: Mar. 7, 2014

(87) PCT Pub. No.: WO2013/038288
PCT Pub. Date: Mar. 21, 2013

(65) Prior Publication Data
US 2014/0221728 A1    Aug. 7, 2014

Related U.S. Application Data (60) Provisional application No. 61/534,407, filed on Sep. 14, 2011.

(51) Int. Cl.
*A61G 11/00* (2006.01)
*A61B 5/00* (2006.01)
(Continued)

(52) U.S. Cl.
CPC ............ *A61G 11/00* (2013.01); *A61B 5/0077* (2013.01); *A61B 5/02427* (2013.01);
(Continued)

(58) Field of Classification Search
CPC ....... A61G 11/00–11/009; A61G 10/00–10/04; A61F 2013/15162
(Continued)

(56) References Cited

U.S. PATENT DOCUMENTS 3,718,078 A * 2/1973 Plummer ................. G02B 3/08
264/2.5
3,809,065 A * 5/1974 Gatts ...................... A61G 11/00
600/22
(Continued)

FOREIGN PATENT DOCUMENTS

CN    201189259 Y    2/2009
CN    201308727 Y    9/2009
(Continued)

*Primary Examiner* — Catherine B Kuhlman (57) ABSTRACT

Monitoring of infants in an incubator may use cameras to measure vital signs and other medical parameters, including oxygen saturation of arterial blood. However, the images obtained by these cameras suffer from a reduced signal-to-noise ratio due to specular reflectance from light reflecting off the skin of the infant. By including radiation scattering structures within the incubator walls and light sources arranged along the edges of the incubator walls, diffuse illumination may be achieved, specular reflectance may be reduced, and the above-mentioned adverse affects on the signal-to-noise ratio of the camera images may be avoided and/or reduced.

10 Claims, 6 Drawing Sheets

(51) Int. Cl.
 *A61B 5/024* (2006.01)
 *A61B 5/1455* (2006.01)
 *G01G 19/44* (2006.01)
 *A61B 5/0205* (2006.01)
 *A61B 5/08* (2006.01)

(52) U.S. Cl.
 CPC ....... *A61B 5/14552* (2013.01); *G01G 19/445* (2013.01); *A61B 5/02055* (2013.01); *A61B 5/0816* (2013.01); *A61B 2503/045* (2013.01); *A61G 2203/44* (2013.01); *A61G 2203/46* (2013.01); *A61G 2210/30* (2013.01)

(58) Field of Classification Search
 USPC ...... 600/21–22; 359/591–598, 599, 601–615
 See application file for complete search history.

(56) References Cited

U.S. PATENT DOCUMENTS

| | | | |
|---|---|---|---|
| 6,872,220 | B2 | 3/2005 | Williams et al. |
| 8,251,561 | B2 | 8/2012 | Montgomery |
| 2004/0068305 | A1* | 4/2004 | Bansal ................. A61N 5/0621 607/89 |
| 2010/0172152 | A1* | 7/2010 | Boonekamp .......... F21V 7/0008 362/609 |
| 2010/0309688 | A1 | 12/2010 | Montgomery et al. |
| 2014/0078301 | A1* | 3/2014 | Fazzi ................... A61B 5/0059 348/143 |

FOREIGN PATENT DOCUMENTS

| | | |
|---|---|---|
| WO | 02093312 A2 | 11/2002 |
| WO | 03030801 A2 | 4/2003 |
| WO | 2005101070 A1 | 10/2005 |

* cited by examiner

INCUBATOR ILLUMINATION

The present disclosure pertains to systems and methods for providing illumination for a camera, and, in particular, to provide diffuse illumination for a (monitoring) camera in an incubator.

It is well known that incubators are indispensable to keep infants, including neonates, safe, warm, comfortable, and/or healthy, especially in NICU environments. It is well known that an infant's vital signs, including temperature, heart rate, and/or respiratory rate, as well as an infant's saturation of peripheral oxygen, provide important medical information for a healthcare provider. It is well known that (digital) cameras may be used for monitoring infants, in conjunction with analytical and/or diagnostic programs and/or software to (help) interpret images from the camera. It is well known that specular reflectance in a camera's digital image adversely impacts the signal-to-noise ratio, and thus the amount of useful information contained within the image.

Accordingly, it is an object of one or more embodiments of the present disclosure to provide an incubator system configured to provide illumination for one or more cameras. The incubator system comprises a plurality of walls, one or more sensors, one or more light sources, one or more processors, a positioning module and a light module. The walls may form a cavity and be substantially transparent, and individual walls may include a surface that faces into the cavity, a surface that faces away from the cavity, and edges along top, bottom, and sides. At least two of the walls include radiation scattering structures arranged to scatter electromagnetic radiation guided within the wall through the surface that faces into the cavity such that at least part of the cavity is illuminated diffusely. The one or more sensors may generate one or more output signals conveying information related to a position of an infant within the cavity. The one or more light sources may be configured such that electromagnetic radiation emitted by a light source is guided into a wall that includes the radiation scattering structures. The positioning module may be configured to determine the position of an infant within the cavity, wherein the determination is based on information from the one or more sensors. The light module may be configured to control the one or more light sources based on the determined position of the infant such that electromagnetic radiation emitted by the one or more light sources impacts specular reflectance observed through at one camera in a specific manner. The specific manner of impacting specular reflectance may be to reduce specular reflectance and/or increase signal-to-noise ratio.

It is yet another aspect of one or more embodiments of the present disclosure to provide a method for providing illumination for one or more cameras in an incubator system. The system comprises forming a cavity using a plurality of walls, the walls being substantially transparent, wherein at least two of the plurality of walls include radiation scattering structures arranged to scatter electromagnetic radiation guided within the wall through a surface that faces into the cavity such that at least part of the cavity is illuminated diffusely; generating one or more output signals conveying information related to a position of an infant within a cavity; determining the position of an infant within the cavity; emitting electromagnetic radiation by one or more light sources such that the electromagnetic radiation is guided into one of the walls that includes the radiation scattering structures; and controlling the emission of electromagnetic radiation based on the determined position of the infant such that specular reflectance observed through at least one camera is impacted in a specific manner. The individual walls may include (i) a surface that faces into the cavity, (ii) a surface that faces away from the cavity, and (iii) edges along top, bottom and sides. The specific manner of impacting the specular reflectance may pertain to the emitted electromagnetic radiation substantially having an angle of incidence with at least one camera of less than 40 degrees.

It is yet another aspect of one or more embodiments to provide a system configured for providing illumination for one or more cameras in an incubator system. The system comprises plurality of substantially transparent means for forming a cavity, wherein individual means include (i) a surface that faces into the cavity, (ii) a surface that faces away from the cavity, and (iii) edges along top, bottom and sides, wherein at least two of the plurality of means for forming the cavity include structures arranged to scatter electromagnetic radiation guided within the means for forming the cavity through the surface that faces into the cavity such that at least part of the cavity is illuminated diffusely; means for generating one or more output signals conveying information related to a position of an infant within a cavity; means for determining the position of an infant within the cavity; means for emitting electromagnetic radiation such that the electromagnetic radiation is guided into one of the means for forming the cavity that includes the radiation scattering structures; and means for controlling the emission of electromagnetic radiation based on the determined position of the infant such that specular reflectance observed through at least one camera is impacted in a specific manner.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals may designate corresponding parts in the various figures. It is to be expressly understood, however, that the drawings are for the purpose of illustration and description only and are not intended as a definition of any limits.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
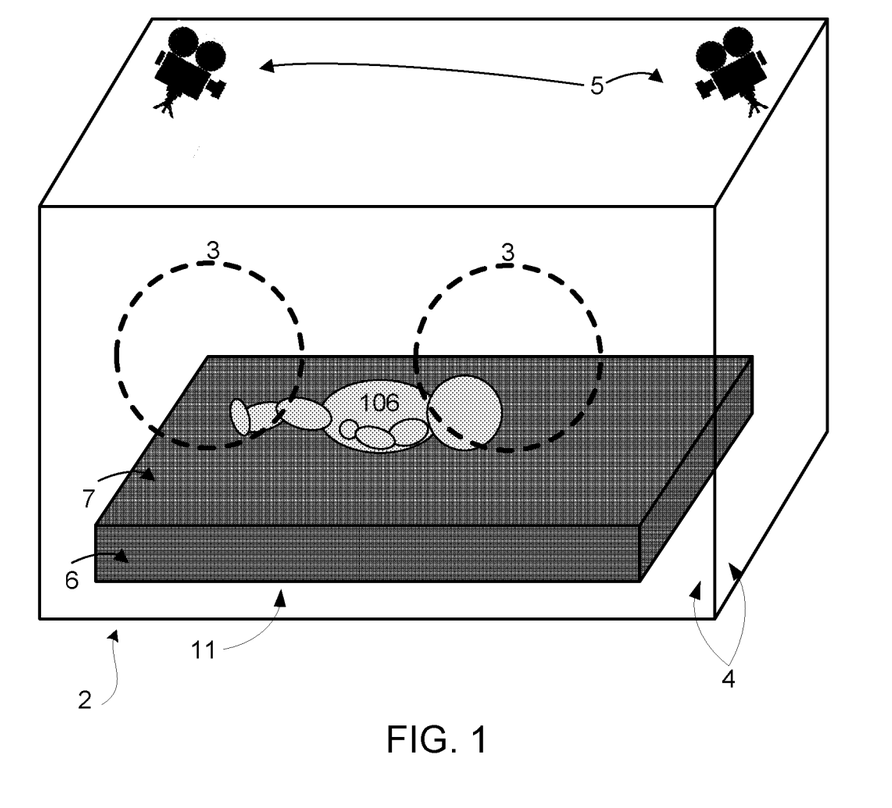
FIG. 1 illustrates an incubator.

FIG. 1 illustrates an incubator 2. Incubator 2 may be configured to protect and/or warm a subject, such as, e.g. infant 106. Incubator 2 may include a subject support structure 6, transparent walls 4 forming a cavity 11, access windows 3, one or more cameras 5, and/or other components. Subject support structure 6 may include, e.g., a mattress. Subject support structure 6 may be interchangeably referred to as mattress 6 throughout. Mattress 6 may include a top surface 7 that engages infant 106 during use of incubator 2. Incubator 2 may include one or more of a heater, a thermometer, a light source, and/or other components (not shown in FIG. 1). Commonly, one or more light sources may be used to provide illumination for the one or more cameras 5. Associated light fixtures and/or associated wiring arranged in and/or near the incubator may be obtrusive and/or inconvenient to healthcare providers.

Infant 106 may be monitored while in incubator 2. One or more cameras may be used to monitor vital signs, including temperature, heart rate, and/or respiratory rate, as well as the infant's oxygen saturation of arterial blood ($SpO_2$), whether peripheral or central. Cameras may be used to measure and/or monitor other parameters related to the status of infant 106. Camera monitoring and/or measuring may be used as a contact-less, non-invasive means to obtain information. "Contact-less" refers to either refraining from the use of adhesives (e.g. on the skin) and/or refraining from direct skin contact in the context of this disclosure. Research has shown, through e.g. modeling, that specular reflectance may adversely impact the signal-to-noise ratio of a (digital) camera image. For the purposes of this disclosure, noise may be the unwanted, unuseful, and/or uninformative components of a camera image. In some embodiments, the noise-level and signal-level of a (part of a) camera image may be determined according to standard mechanisms known in the art of digital image processing. In some embodiments, the image artifacts caused by specular reflectance may be classified as noise. As such, diffuse illumination may be desirable for illumination purposes. Diffuse illumination may also be desirable as it allows a higher intensity of illumination without shining light directly into an infant's eyes. Note that premature infants may naturally prefer an environment as dark as the womb they were supposed to be in. In some embodiments only (part of) the exposed skin of infant 106 needs to be illuminated for a camera, since, e.g., $SpO_2$ may not typically be monitored through clothing.

Referring to FIG. 1, one or more light sources that are used for illumination may be used for phototherapy, e.g. to treat jaundice. Commonly-used light fixtures may be mounted at and/or near the top of an incubator and may thus be obtrusive and/or inconvenient to healthcare providers.

Figure 3A:
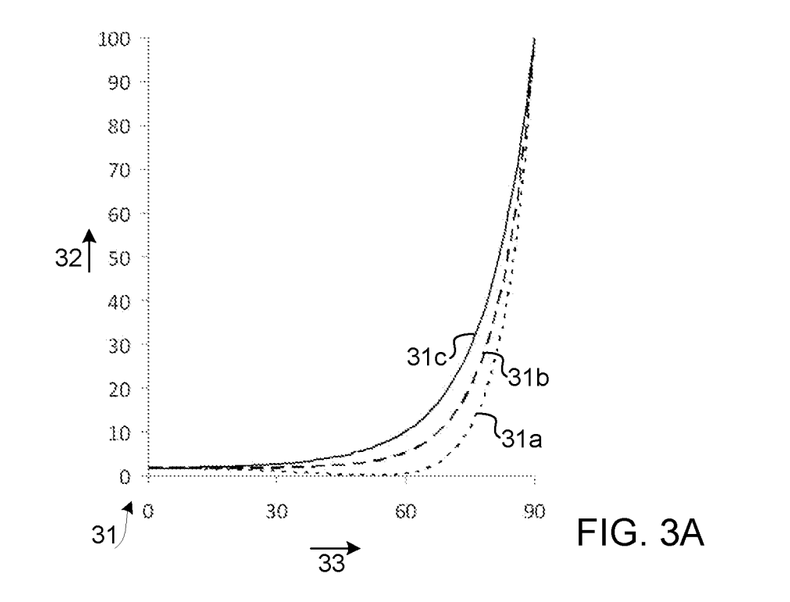
FIGS. 3A, 3B and 3C illustrates various modeled graphs involving specular reflectance and/or $SpO_2$ measurements.
Figure 3B:
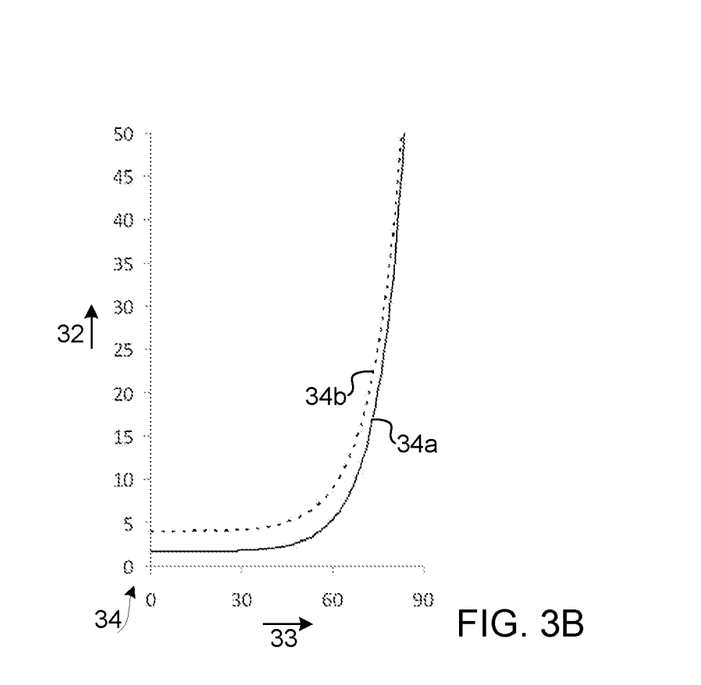

Research has shown, through e.g. modeling, that specular reflectance generally increases as the angle of incidence between light source and observer (e.g., a camera) increases, though the increase is more dramatic for angles greater than roughly 40 degrees. Depending on the refractive index n of the surface (e.g., the skin of an infant), and further depending on the use and/or type of polarization, the so-called knee of the reflectance-angle of incidence curve may move slightly. By way of illustration, FIG. 3A illustrates graph 31 depicting the specular reflectance coefficient 32 (as a percentage, on the Y-axis) according to Fresnel equations (for a refractive index transition from air to water, or n=1 to n=1.3) for an angle of incidence 33 (on the X-axis) ranging from 0 to 90 degrees. Graph 31b represents the unpolarized specular reflectance, graph 31a represents perpendicular specular reflectance, and graph 31c represents parallel specular reflectance. By further way of illustration, FIG. 3B illustrates graph 34 depicting specular reflectance coefficient 32 (unpolarized, as a percentage, on the Y-axis) according to Fresnel equations (for a refractive index transition 34a from air to water, or n=1 to n=1.3, and a transition 34b from air to oily skin, or n=1 to n=1.5) for an angle of incidence 33 (on the X-axis) ranging from 0 to 90 degrees. Transition graphs 34a and 34b illustrates that specular reflectance coefficient 32 appears substantially constant for an angle of incidence 33 between 0 and, approximately, 40 degrees.

An acceptable threshold level of specular reflectance may be 3%, 4%, 5%, 6%, 7%, 8%, 10%, or another threshold level of specular reflectance. As a result, corresponding acceptable angles of incidence (see FIG. 3A and FIG. 3B) may be 30 degrees, 35 degrees, 40 degrees, 45 degrees, 50 degrees, and/or another threshold for angle of incidence, depending on conditions (e.g. the refractive index transition, polarization, etc.).

Figure 3C:
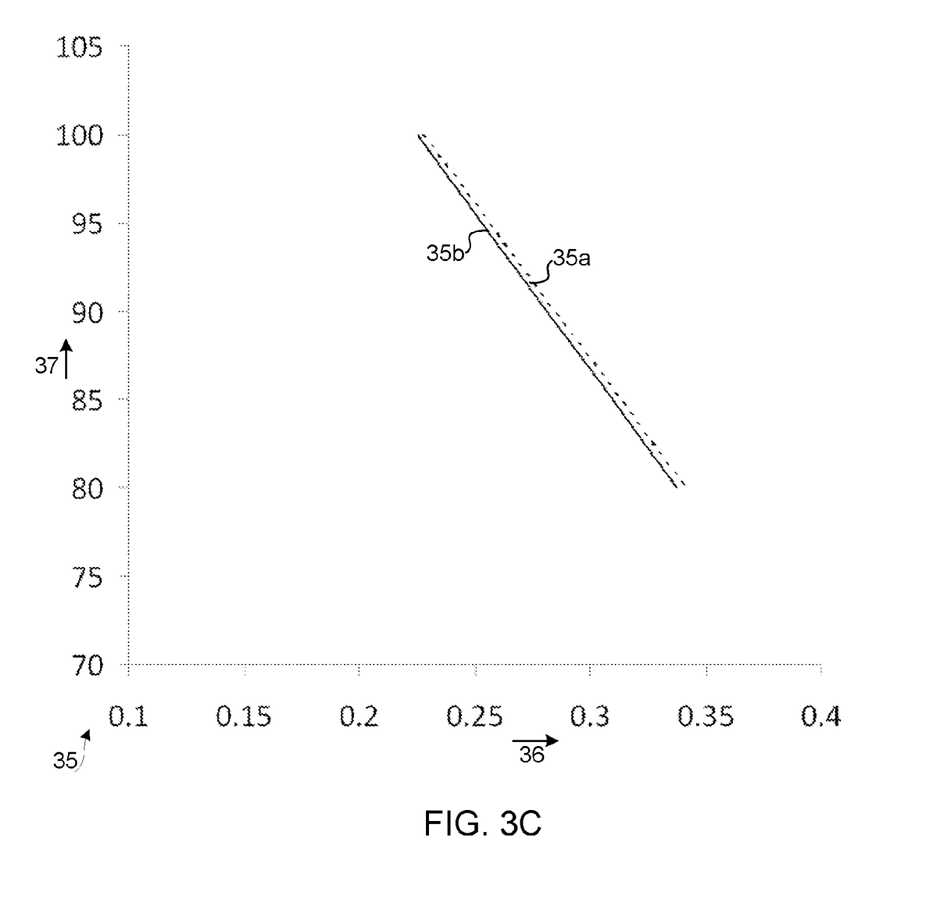

Research has shown, through e.g. modeling, that the intensity of reflected light during photo-plethysmography includes an alternating part ("AC") that alternates according to the heart rate and a non-modulated part ("DC") that may be corrupted by specular reflectance. The ratio of these parts may vary with the specular reflectance, which in turn may corrupt and/or disturb the $SpO_2$ calibration curves. By way of illustration, FIG. 3C illustrates graph 35 depicting the calibration discrepancy 37 (as a percentage of $SpO_2$, on the Y-axis) for a given ratio 36 of the AC and DC (on the X-axis), for a particular frequency/color of electromagnetic radiation/light. Graph 35a corresponds to a specular reflectance of 6%, whereas graph 35b corresponds to a specular reflectance of 0%.

Note that electromagnetic radiation emitted by real-world light sources, as opposed to simplistic theoretical models of light sources, may have a non-deterministic distribution of its intensity and/or (beam) direction, at least for practical applications of digital image processing. Note furthermore that scattering a beam of electromagnetic radiation may be considered a stochastic event governed by a probability distribution. Nonetheless, scattered electromagnetic radiation may be considered to substantially have a particular angle of incidence at or near a particular location (e.g. with a camera) if at least about 70%, at least about 80%, about 90%, and/or another percentage of the observed radiation has that particular angle of incidence or a smaller angle of incidence.

Figure 2:
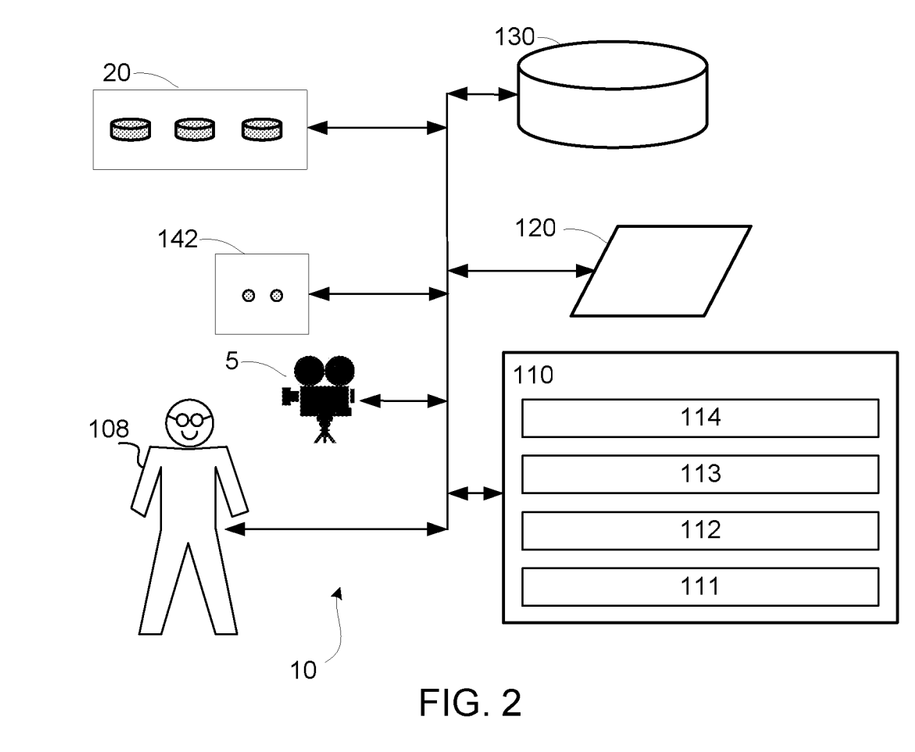
FIG. 2 schematically illustrates components of an incubator system in accordance with one or more embodiments described herein.

FIG. 2 schematically illustrates components of an incubator system 10 in accordance with one or more embodiments described herein, configured to provide illumination for one or more cameras 5. The one or more cameras may operate in conjunction with incubator system 10. The one or more cameras may be integrated within incubator system 10, and/or may be discrete and separate devices from incubator system 10. Incubator system 10 may include a plurality of walls 4 which may form a cavity 11, one or more sensors 142, one or more light sources 20, a user interface 120, an electronic storage 130, one or more processors 110, and/or other components.

Individual walls 4 may include a surface that faces into cavity 11, a surface that faces away from cavity 11, and edges along top bottom and sides of individual walls 4. At least two of the plurality of walls 4 may include radiation scattering structures arranged to scatter electromagnetic radiation (e.g., visible light) guided within an individual wall 4 substantially through the surface that faces into cavity 11 such that at least part of cavity 11 may be illuminated diffusely. This substantial scattering may imply that the amount of energy of the electromagnetic radiation scattered through the surface that faces into cavity 11 is greater than the amount of energy of the electromagnetic radiation scattered through the surface that faces away from cavity 11. The substantial scattering may not imply what portion of electromagnetic radiation emitted from a light source 20 may be guided within a wall 4, nor what portion may pass through wall 4 without being scattered. In some embodiments, scattering of electromagnetic radiation through a surface that faces away from cavity 11 may be reduced by applying a reflective coating on such a surface Individual walls 4 may include glass, plastic, Plexiglas™, and/or other substantially transparent materials, or any combination thereof.

The radiation scattering structures may include one or both of non-uniformities within an individual wall 4, and/or non-uniformities on a surface of individual wall 4. As a non-limiting example, radiation scattering structures may include particles, bubbles, droplets, density fluctuations, crystallites, defects, surface roughness, reflective surfaces, etchings, and/or other structures or features arranged to scatter electromagnetic radiation, or any combination thereof. In some embodiments, scattering structures, e.g. etchings, may be arranged and/or designed to scatter electromagnetic radiation at different heights within an individual wall 4, going through a surface of an individual wall 4 at different angles (i.e. aiming up, down, left, right, and/or other directions, and/or any combination thereof), and/or going through a surface of an individual wall 4 at different degrees of diffusion.

Figure 4A:
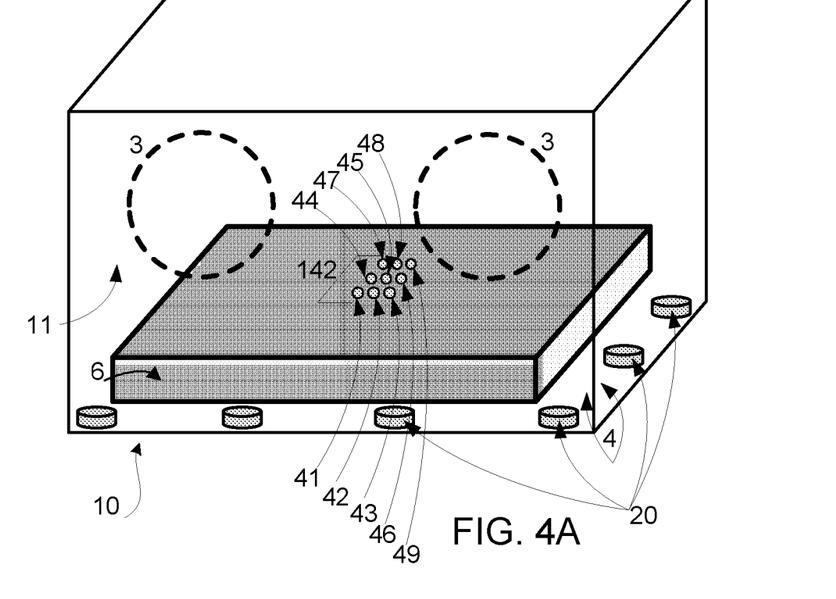
FIGS. 4A and 4B illustrate an incubator system in accordance with one or more embodiments described herein.
Figure 4B:
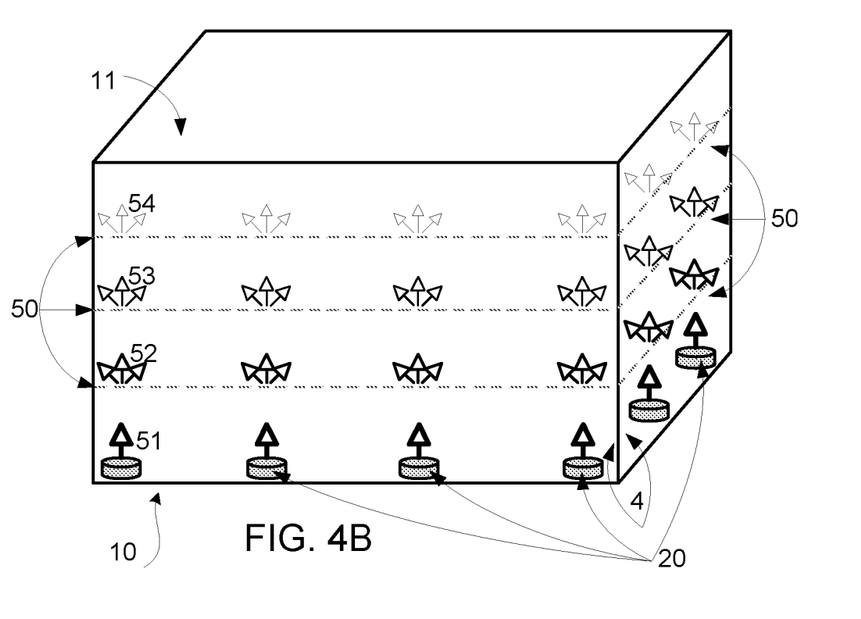

By way of illustration, FIG. 4B illustrates various aspects of incubator system 10 in accordance with one or more embodiments described herein. As with FIG. 1, a cavity 11 is formed by multiple substantially transparent walls 4. An infant 106 (not shown in FIG. 4B) may be placed within cavity 11. Light sources 20 may be arranged such that emitted electromagnetic radiation, such as, e.g., light 51, may be substantially guided into a wall 4, which may imply that the majority of the amount of energy of the electromagnetic radiation emitted by an individual light source 20 is guided into a wall 4. Referring to FIG. 4B, in the embodiment depicted in FIG. 4B, light sources 20 are arranged along the bottom edge of individual walls 4. The positioning, orientation, direction, angle, and/or number of light sources 20 depicted in FIG. 4B are meant to be exemplary, not limiting. For example, one or more light sources 20 may alternatively, and/or simultaneously, be arranged along the top edge of an individual wall 4, and/or along the side edges of an individual wall 4. In the latter case, the electromagnetic radiation emitted from a light source 20 arranged along the side edge of an individual wall 4 may be oriented substantially horizontally (prior to scattering), rather than substantially vertically (prior to scattering). In some embodiments, the number of light sources 20 arranged along the bottom edge of an individual wall may be much larger (e.g. 10, 20, 50, 100, 500, 1000, or another number) than depicted in FIG. 4A and FIG. 4B, with corresponding fine-grained control from a light module. Note that light sources 20, and/or wiring associated with light sources 20, may be arranged outside of cavity 11 and may thus be unobtrusive for healthcare providers.

Walls 4 in incubator system 10 in FIG. 4B include radiation scattering structures 50 (interchangeably referred to herein as scattering structures 50) arranged to scatter electromagnetic radiation guided within wall 4. Scattering of light 51 at scattering locations 52, 53, and 54 is depicted by progressively smaller arrows indicating a smaller amount of energy of the electromagnetic radiation at or near the indicated location. Scattered electromagnetic radiation may be emitted through a surface of wall 4, in particular through the surface that faces into cavity 11. Scattering structures 50 may be arranged such that at least part of cavity 11 is illuminated diffusely by the scattered electromagnetic radiation. Though radiation scattering structures 50, in the embodiment depicted in FIG. 4B, appear to be arranged in line with an individual light source 20, this is merely an exemplary embodiment, and not meant to be limiting. Though radiation scattering structures 50, in the embodiment depicted in FIG. 4B, appear to be arranged at similar heights along and/or within wall 4 for different light sources 20, this is merely an exemplary embodiment, and not meant to be limiting. For example, in some embodiments, scattering structures 50 may be arranged at different heights along individual walls 4, such that different light sources 20 are configured to illuminate a different area within cavity 11 through scattering of electromagnetic radiation by scattering structures 50 at different heights.

Sensor(s) 142 of incubator system 10 in FIG. 2 may be configured to generate output signals conveying information related to the status of infant 106, medical parameters related to infant 106, the environment within cavity 11, and/or other information. As a non-limiting example, sensors 142 may generate one or more output signals conveying information related to a (three-dimensional) position of infant 106 within cavity 11, e.g. through stereoscopy. Sensors 142 may include one or more of a temperature sensor, a weight sensor, one or more still-image cameras, one or more video cameras, and/or other sensors.

The illustration of sensor 142 including two members in FIG. 2 is not intended to be limiting. Incubator system 10 may include a single sensor. In some embodiments sensor 142 includes a plurality of more than two sensors operating as described above by generating output signals conveying information related to parameters associated with the state and/or condition of infant 106, cavity 11, the breathing of infant 106, the gas breathed by infant 106, the heart rate of infant 106, the respiratory rate of infant 106, and/or other parameters. Resulting signals or information from sensor 142 may be transmitted to processor 110, user interface 120, electronic storage 130, and/or other components of incubator system 10. This transmission can be wired and/or wireless.

One or more light sources 20 of incubator system 10 in FIG. 2 may be configured such that electromagnetic radiation emitted by the one or more light sources is guided into one of the walls that include the scattering structures. Light sources may be arranged along the top edge, the bottom edge, and/or the side edges of an individual wall 4, or any combination thereof. Light sources 20 may be configured to have a controllable level of intensity, a controllable direction and/or angle of illumination, a controllable selection of illumination spectra, and/or other controllable illumination characteristics and/or illumination parameters. For example, illumination parameters of a light source 20 may be controlled by adjusting optical components within the light source, including, but not limited to, one or more of refractive components, reflective components, lenses, mirrors, filters, polarizers, diffraction gradients, optical fibers, and/or other optical components. Individual light sources 20 may be controlled such that only part of the exposed skin of infant 106 is illuminated for a camera, while everything else within cavity 11 may be kept as dark as possible.

User interface 120 of incubator system 10 in FIG. 2 may be configured to provide an interface between incubator system 10 and a user (e.g., user 108, a caregiver, a healthcare provider, a therapy decision-maker, etc.) through which the user can provide information to and receive information from incubator system 10. This enables data, results, and/or instructions and any other communicable items, collectively referred to as "information," to be communicated between the user and incubator system 10. An example of information that may be conveyed to user 108 is a report detailing the changes in monitored vital signs throughout a period during which infant 106 is present within incubator system 10. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 by user interface 120 in the form of auditory signals, visual signals, tactile signals, and/or other sensory signals, or any combination thereof.

By way of non-limiting example, user interface 120 may include a radiation source capable of emitting light. The radiation source may include, for example, one or more of at least one LED, at least one light bulb, a display screen, and/or other sources. User interface 120 may control the radiation source to emit light in a manner that conveys to user 108 information related to the determined level of $SpO_2$.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into incubator system 10 from removable storage (e.g., a smart card, a flash drive, a removable disk, etc.) that enables the user(s) to customize the implementation of incubator system 10. Other exemplary input devices and techniques adapted for use with incubator system 10 as user interface 120 include, but are not limited to, an RS-232 port, RF link, an IR link, modem (telephone, cable, Ethernet, internet or other). In short, any technique for communicating information with incubator system 10 is contemplated as user interface 120.

Electronic storage 130 of incubator system 10 in FIG. 2 comprises electronic storage media that electronically stores information. The electronic storage media of electronic storage 130 may include one or both of system storage that is provided integrally (i.e., substantially non-removable) with incubator system 10 and/or removable storage that is removably connectable to incubator system 10 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables incubator system 10 to function properly. For example, electronic storage 130 may record or store one or more vital signs (as discussed elsewhere herein), $SpO_2$ measurements, and/or other information. Electronic storage 130 may be a separate component within incubator system 10, or electronic storage 130 may be provided integrally with one or more other components of incubator system 10 (e.g., processor 110).

Processor 110 of incubator system 10 in FIG. 2 is configured to provide information processing capabilities in incubator system 10. As such, processor 110 includes one or more of a digital processor, an analog processor, a digital circuit designed to process information, an analog circuit designed to process information, a state machine, and/or other mechanisms for electronically processing information. Although processor 110 is shown in FIG. 2 as a single entity, this is for illustrative purposes only. In some implementations, processor 110 includes a plurality of processing units.

As is shown in FIG. 2, processor 110 is configured to execute one or more computer program modules. The one or more computer program modules include one or more of a parameter determination module 111, a positioning module 112, a light module 113, a camera interface 114, and/or other modules. Processor 110 may be configured to execute modules 111, 112, 113, and/or 114 by software; hardware; firmware; some combination of software, hardware, and/or firmware; and/or other mechanisms for configuring processing capabilities on processor 110.

It should be appreciated that although modules 111, 112, 113, and 114 are illustrated in FIG. 2 as being co-located within a single processing unit, in implementations in which processor 110 includes multiple processing units, one or more of modules 111, 112, 113, and/or 114 may be located remotely from the other modules. The description of the functionality provided by the different modules 111, 112, 113, and/or 114 described below is for illustrative purposes, and is not intended to be limiting, as any of modules 111, 112, 113, and/or 114 may provide more or less functionality than is described. For example, one or more of modules 111, 112, 113, and/or 114 may be eliminated, and some or all of its functionality may be provided by other ones of modules 111, 112, 113, and/or 114. Note that processor 110 may be configured to execute one or more additional modules that may perform some or all of the functionality attributed below to one of modules 111, 112, 113, and/or 114.

Parameter module 111 of incubator system 10 in FIG. 2 may be configured to determine one or more status parameters, medical parameters, and/or other parameters from output signals generated by sensor(s) 142. One or more status parameters may be related to the presence and/or position of infant 106 within cavity 11. One or more medical parameters may be related to monitored vital signs of infant 106, and/or other medical parameters of infant 106. Other parameters may be related to the environment inside or outside cavity 11, such as, e.g., air temperature within the cavity. Some or all of this functionality may be incorporated or integrated into other computer program modules of processor 110.

Positioning module 112 of incubator system 10 in FIG. 2 may be configured to determine the presence, (three-dimensional) position, and/or orientation of infant 106 (and/or anatomical parts including but not limited to one or more legs, one or more arms, head, forehead, and/or other anatomical parts of infant 106) within cavity 11. The determination by positioning module 112 may be based on information from sensors 142, such as information from, e.g., one or more weight sensors, and/or through stereoscopy using multiple cameras. In some embodiments, positioning module 112 may be configured to determine in which area (and/or in which orientation) within cavity 11 the exposed skin of infant 106, e.g. the head or feet of the infant, is currently located, such that light sources 20 may be controlled accordingly.

By way of illustration, FIG. 4A illustrates various aspects of incubator system 10 in accordance with one or more embodiments described herein. As with FIG. 1, a cavity 11 is formed by multiple substantially transparent walls 4, some of which may have access windows 3. An infant 106 (not shown in FIG. 4A) may be supported by mattress 6. Light sources 20 may be arranged to such that emitted electromagnetic radiation may be substantially guided into a wall 4, which may imply that the majority of the amount of energy of the electromagnetic radiation emitted by an individual light source 20 may be guided into a wall 4. Referring to FIG. 4A, in the embodiment depicted in FIG. 4A, sensors 142 may be arranged, e.g. as a grid of nine weight sensors 41-49, and/or in any other regular or irregular pattern. The number of weight sensors depicted in FIG. 4A is meant to be exemplary, not limiting. The placement of weight sensors 41-49 on or near mattress 6 is meant to be exemplary, not limiting. In some embodiments, positioning module 12 may be configured to determine the presence, position and/or orientation of infant 106 within cavity 11 based on the weight information conveyed through the output signals generated by weight sensors 41-49.

Light module 113 of incubator system 10 in FIG. 2 may be configured to control one or more light sources 20 based on the determined position of infant 106 such that electromagnetic radiation emitted by the one or more light sources impacts specular reflectance observed through at least one camera in a specific manner. The specific manner of impacting specular reflectance may be to increase the signal-to-noise ratio for images taken by a particular camera, and/or may pertain to another consequence or altering the specular reflectance in or near cavity 11. Control by light module 113 may be based on individual light sources, groups of light sources, and/or both. Control by light module 113 may include control of the controllable level of intensity, the controllable direction and/or angle of illumination, the controllable selection of illumination spectra, and/or other controllable illumination characteristics and/or illumination parameters of one or more light sources 20. In some embodiments, radiation scattering structures 50 may be arranged at different heights along individual walls 4, such that different light sources 20 are configured to illuminate a different area within cavity 11 through scattering of electromagnetic radiation by scattering structures 50 at different heights. Control by light module 113 may be based on information from positioning module 112.

Control of multiple (groups of) light sources 20 may be coordinated and/or synchronized to accomplish impacting the specular reflectance observed through at least one camera in a specific manner. For example, light module 113 may establish a baseline control setting for multiple light sources 20 and determine, e.g. using output signals from sensors 142, a corresponding baseline specular reflectance measurement for a particular camera (or a set of such measurements for a set of cameras). Alternatively, and/or simultaneously, the determined corresponding baseline specular reflectance measurement may be based on information from one or more cameras as provided, e.g., through camera interface module 114. The baseline specular reflectance measurement may be used to compare and/or verify whether a change in the control settings corresponds to an improved specular reflectance measurement.

Light module 113 may be configured to control a set of light sources 20 such that a particular threshold of specular reflectance is achieved for a particular camera, such that the set of light sources use an illumination spectrum suitable for, e.g., SpO2 measurements. Alternatively, and/or simultaneously, light module 113 may be configured to control a second set of light sources 20 such that a threshold level of phototherapy, e.g. for jaundice, is administered to infant 106, using an illumination spectrum suitable for such phototherapy.

Camera interface module 114 of incubator system 10 in FIG. 2 may be configured to provide an interface between one or more cameras and incubator system 10. Camera interface module 114 may be used to provide external (camera) information, such as e.g. one or more specular reflectance measurements for one or more cameras, to other modules within incubator system, such as, e.g., light module 113.

Figure 5:
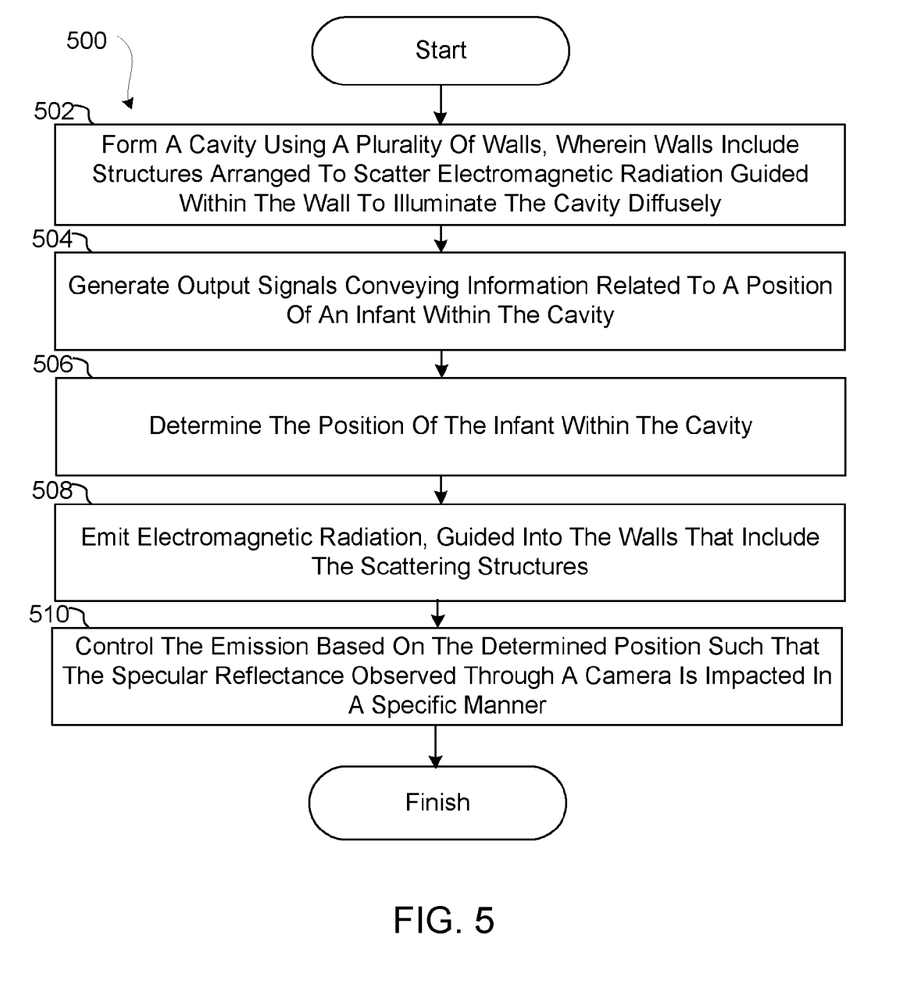
FIG. 5 illustrates a method for providing illumination for one or more cameras in an incubator system.

FIG. 5 illustrates a method 500 for providing illumination for one or more cameras in an incubator system. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, a cavity is formed using a plurality of substantially transparent walls, wherein at least some of the walls include scattering structures arranged to scatter electromagnetic radiation guided within the wall to illuminate (part of) the cavity diffusely. In one embodiment, operation 502 is performed by a plurality of walls similar to or substantially the same as walls 4 (shown in FIG. 4 and described above).

At an operation 504, output signals are generated conveying information related to a position of an infant (in particular exposed skin of the infant) within the cavity. In one embodiment, operation 504 is performed by one or more sensors similar to or substantially the same as sensors 142 (shown in FIG. 4 and described above).

At an operation 506, the position of the infant within the cavity is determined. In one embodiment, operation 506 is performed by a positioning module similar to or substantially the same as positioning module 112 (shown in FIG. 4 and described above).

At an operation 508, electromagnetic radiation is emitted, such that the electromagnetic radiation is guided into the walls that include the scattering structures. In one embodiment, operation 508 is performed by one or more light sources similar to or substantially the same as light sources 20 (shown in FIG. 4 and described above).

At an operation 510, the emission of electromagnetic radiation is controlled based on the determined position of the infant within the cavity, such that the specular reflectance observed through at least one camera is impacted in a specific manner. The specific manner of impacting the specular reflectance may pertain to increasing the signal-to-noise ratio of images captured by the at least one camera, for example by reducing the angle of incidence with the at least one camera to less than substantially 40 degrees. In one embodiment, operation 510 is performed by a light module similar to or substantially the same as light module 113 (shown in FIG. 4 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. An incubator system configured to provide illumination for one or more cameras, comprising:
   a plurality of walls forming a cavity, the walls being substantially transparent, wherein the individual walls include
      (i) a surface that faces into the cavity,
      (ii) a surface that faces away from the cavity, and
      (iii) edges along top, bottom and sides,
   wherein at least two of the plurality of walls includes radiation scattering structures arranged to scatter electromagnetic radiation, the scattered electromagnetic radiation being guided within the wall and being guided out into the cavity through the surface that faces into the cavity, such that at least part of the cavity is illuminated diffusely;
   one or more sensors that generate one or more output signals conveying information related to a position of an infant within the cavity;
   one or more light sources configured such that electromagnetic radiation emitted by the one or more light sources is guided into one of the walls that includes the radiation scattering structures; and
   one or more processors configured to execute computer program modules, the computer program modules comprising:
      a positioning module configured to determine the position of an infant within the cavity, wherein the determination is based on information from the one or more sensors; and
      a light module configured to control the one or more light sources based on the determined position of the infant such that electromagnetic radiation emitted by the one or more light sources impacts specular reflectance observed through at least one camera by affecting an incidence angle between the one or more light sources and the at least one camera.

2. The incubator system of claim 1, wherein the one or more sensors include one or more weight sensors, and wherein the determination by the positioning module is based on information from the one or more weight sensors.

3. The incubator system of claim 1, wherein control of the one or more light sources by the light module includes control of one or both of an illumination intensity and/or an illumination direction of at least one light source.

4. The incubator system of claim 1, wherein the radiation scattering structures included in a wall include one or both of non-uniformities within the wall and/or non-uniformities on a surface of the wall.

5. The incubator system of claim 1, wherein affecting the incidence angle between the one or more light sources and the at least one camera includes the electromagnetic radiation emitted by the one or more light sources substantially having an angle of incidence between the one or more light sources and the at least one camera of less than 40 degrees.

6. A method to provide illumination for one or more cameras in an incubator system, the method comprising:
   forming a cavity using a plurality of walls, the walls being substantially transparent, wherein the individual walls include
      (i) a surface that faces into the cavity,
      (ii) a surface that faces away from the cavity, and
      (iii) edges along top, bottom and sides,
   wherein at least two of the plurality of walls includes radiation scattering structures arranged to scatter electromagnetic radiation, the scattered electromagnetic radiation being guided within the wall and being guided out into the cavity through the surface that faces into the cavity, such that at least part of the cavity is illuminated diffusely;
   generating one or more output signals conveying information related to a position of an infant within a cavity;
   determining the position of an infant within the cavity;
   emitting electromagnetic radiation by one or more light sources such that the electromagnetic radiation is guided into one of the walls that includes the radiation scattering structures; and
   controlling the emission of electromagnetic radiation based on the determined position of the infant such that the electromagnetic radiation impacts specular reflectance observed through at least one camera by affecting an incidence angle between the one or more light sources and the at least one camera.

7. The method of claim 6, wherein the one or more sensors include one or more weight sensors, and wherein the determination of the position of the infant is based on information from the one or more weight sensors.

8. The method of claim 6, wherein controlling the emission of electromagnetic radiation includes controlling of one or both of an illumination intensity and/or an illumination direction of at least one light source.

9. The method of claim 6, wherein the radiation scattering structures included in a wall include one or both of non-uniformities within the wall and/or non-uniformities on a surface of the wall.

10. The method of claim 6, wherein affecting the incidence angle between the one or more light sources and the at least one camera includes the emitted electromagnetic radiation substantially having an angle of incidence between the one or more light sources and the at least one camera of less than 40 degrees.

* * * * *